United States Patent [19]

Afonso et al.

[11] Patent Number: 4,540,580

[45] Date of Patent: * Sep. 10, 1985

[54] 2-[(1'R)-1'-AMINOALKYL]PENEMS

[75] Inventors: Adriano Afonso, West Caldwell; Jay Weinstein, Upper Montclair, both of N.J.

[73] Assignee: Schering Corporation, Kenilworth, N.J.

[ * ] Notice: The portion of the term of this patent subsequent to Sep. 10, 2002 has been disclaimed.

[21] Appl. No.: 441,989

[22] Filed: Nov. 16, 1982

[51] Int. Cl.$^3$ .................. C07D 499/00; A61K 31/425
[52] U.S. Cl. ............................. 514/195; 260/245.2 R
[58] Field of Search .................. 260/245.2 R; 424/270

[56] References Cited

U.S. PATENT DOCUMENTS

| | | | |
|---|---|---|---|
| 4,260,618 | 4/1981 | Christensen et al. | 424/263 |
| 4,272,437 | 6/1981 | Menard et al. | 260/245.2 R |
| 4,301,074 | 11/1981 | Christensen et al. | 260/245.2 R |

FOREIGN PATENT DOCUMENTS 2013674 8/1979 United Kingdom .

*Primary Examiner*—Nicholas S. Rizzo
*Attorney, Agent, or Firm*—Anita W. Magatti; Gerald S. Rosen; Stephen I. Miller

[57] ABSTRACT

Disclosed are 6-(1'-hydroxyethyl)-2-[(1'R)-1'-aminoalkyl]penem-3-carboxylic acids and salts and esters thereof. The compounds are useful and potent antibacterial agents and can be formulated into a variety of forms suitable for oral, parenteral or topical use.

29 Claims, No Drawings

2-[(1'R)-1'-AMINOALKYL]PENEMS

BACKGROUND OF THE INVENTION

There is a continuing need for new antibacterials since wide scale usage of any given antibacterial gives rise to resistant strains of pathogens. In addition, the known antibacterials suffer from the disadvantage of being effective only against certain types of microorganisms. Thus, new antibacterial agents are constantly being sought.

Antibacterials of the penem-type are known in the art. See, for instance, U.S. Pat. No. 4,272.437, (1981), U.S. Pat. No. 4,301,074 (1981) and U.S. Pat. No. 4,331,676 (1982).

DESCRIPTION OF THE INVENTION

This invention relates to novel 2-[(1'R)-1'-aminoalkyl]penems and to their use as antibacterial agents. More particularly, this invention concerns the 6-(1hydroxyethyl)-2-[(1'R)-1'-aminoalkyl]penem-3-carboxylic acids represented by the formula

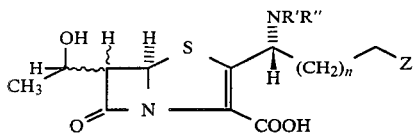

wherein
n is 0–4;
R' and R'' are independently hydrogen, lower alkyl, lower alkenyl, phenyl, substituted phenyl, wherein the substituents are one or more groups selected from chloro, bromo, fluoro, lower alkyl, hydroxy, nitro, amino, aminomethyl, lower monoalkylamino, lower dialkylamino, lower alkoxy and carboxy, or heteroaryl, or R' is hydrogen and R'' is acyl, or R', R'' and the N to which they are attached form an amidino, substituted amidino, or a guanidino group;
Z is hydrogen, COOR', OR', NR'R'', SR', 4-imidazolyl, 3-indolyl, phenyl, p-hydroxyphenyl or branched lower alkyl, and the pharmaceutically acceptable salts and metabolizable esters thereof, in racemic or optically active form.

Preferred compounds of this invention are those represented by the formula

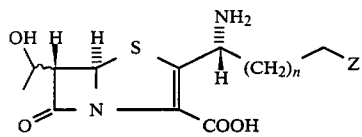

wherein
n is 0–4;
Z is hydrogen, carboxy, hydroxy, (lower)alkylthio or an amino group, and the pharmaceutically acceptable salts and metabolitable esters thereof, in racemic or optically active form.

More preferred are compounds as represented by the formula

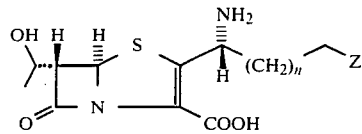

wherein n and Z are as defined for formula Ib

The lower alkyl groups referred to above contain 1–6 carbon atoms and include methyl, ethyl, propyl, butyl, pentyl, hexyl and the corresponding branched chain isomers thereof.

The lower alkenyl groups referred to above contain 2–6, and preferably 2 to 4, carbon atoms, and are, for example, vinyl, allyl, but-2-enyl or but-3-enyl groups.

The term "heteroaryl" as used herein refers to a heterocyclic group of aromatic character which contains 5 to 7 ring atoms of which 3 to 6 are carbon atoms and the remaining ring atoms are nitrogen, sulfur or oxygen atoms. Typical aryl groups are those such as pyridyl, for example, pyrid-2-yl, pyrid-3-yl or pyrid-4-yl, thienyl, for example, thien-2-yl, or furyl, for example, fur-2-yl.

The acyl groups referred to above contain 2–18 carbon atoms and are the residue of sulfonic acid or a carboxylic acid, such as acetyl, propionyl, valeryl and butyryl.

The amidino and substituted amidino groups referred to above are of the formula

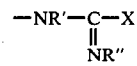

wherein X is hydrogen, lower alkyl or amino and R' and R'' are as defined for formula Ia.

The compounds of the present invention possess 4 asymmetric carbon atoms, indicated in the partial formula II below as the 5, 6, 8 and 1'-position carbon atoms.

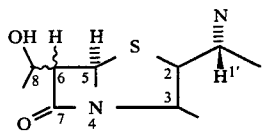

Compounds of the invention may possess 5R,6S,8R,1'R or 5R,6R,8S,1'R stereochemistry at the chiral atoms. The preferred absolute stereochemistry for the compounds of the present invention is 5R,6S,8R,1'R, as represented by formula Ic.

For the purposes of this invention, equivalent to the compounds of formula I are the alkali metal, alkaline-earth metal, amine and acid addition salts, and the metabolizable esters. Examples of the alkali metal and alkaline-earth metal salts are the sodium, potassium, aluminum, magnesium and calcium salts. The amine salts may be formed from a wide variety of suitable organic amines, i.e., aliphatic, cycloaliphatic, (cycloaliphatic) aliphatic or araliphatic primary, secondary or tertiary mono-, di- or polyamines, or heterocyclic bases. Specific examples are those salts derived from triethylamine, 2-hydroxyethylamine, di-(2-hydroxyethyl)amine, tri-(2-hydroxyethyl)amine, 4-aminobenzoic acid 2-diethylaminoethyl ester, 1-ethylpiperidine, bicyclohexylamine, N, N'-dibenzylethylenediamine, pyridine, collidine, quinoline, procaine, dibenzylamine, 1-ephenamine and N-alkylpiperidine. Typical acid addition salts are those formed with mineral acids such as hydrochloric, hydrobromic, hydroiodic, phosphoric, sulfuric or with suitable carboxylic acids or sulfonic acids such as trifluoroacetic, p-toluene sulfonic, maleic, acetic, citric, oxalic, succinic, benzoic, tartaric, fumaric, mandelic, ascorbic and malic. Since the compounds of this invention always contain an acid group (the 3-carboxy group) and a basic group (the 1'-amino group) these groups always form an inner salt, i.e., a Zwitterion. Depending upon the nature of the Z group, they may additionally form the other above described salts. The metabolizable esters are the physiologically cleavable esters, i.e., those esters known in the penicillin, cephalosporin and penem art to be easily cleaved within the body to the parent acid. Examples of such metabolizable esters are those such as indanyl, phthalidyl, methoxymethyl, glycyloxymethyl, phenylglycyloxymethyl, thienylglycyloxymethyl or acyloxymethyl of the formula

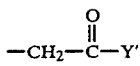

wherein Y' is lower alkyl or phenyl. Particularly preferred esters of this type are methoxymethyl, acetoxymethyl, pivaloyloxymethyl, phthalidyl and indanyl. Preparation of these salts and metabolizable esters may be carried out according to conventional procedures for forming salts of beta-lactam antibiotics such as penicillins and cephalosporins.

Preferred compounds of this invention are those wherein n is 1 and Z is a (lower)alkylthio or a carboxy group.

The compounds of the present invention are useful in view of their pharmacological properties. In particular, they possess antibacterial activity as evidenced by their ability to inhibit the growth of microorganisms.

The antibacterial activity of the instant compounds may be determined by testing in standardized in vitro dilution tests for minimum inhibitory concentrations (MICs). Using such standardized microbiological procedures, the 2-[(1'R)-1'-aminoalkyl]penems of this invention are found to exhibit activity against both gram-positive and gram-negative bacteria such as *Staphylococcus aureus, Escherichia coli* and *Pseudomonas aeruginosa* at test levels of 0.1 to 100 mcg/ml. Additionally, they show activity against such organisms in the presence of penicillinase and cephalosporinase, indicating a resistance to these enzymes.

As antibacterial agents, the compounds of the present invention are conventionally formulated for oral, parenteral, topical and transdermal use. Their zwitterion form is particularly advantageous since it is water-soluble. Thus, the instant invention includes within its scope pharmaceutical compositions comprising the novel compounds of this invention in admixture with a pharmaceutically acceptable carrier therefor. Additionally, the present invention also provides a method of treating bacterial infections in animals, particularly warm-blooded animals, which comprises administering a compound of formulae Ia or Ib or a pharmaceutically acceptable salt or metabolizable ester thereof, or a pharmaceutical composition thereof, to an infected host in an amount sufficient to treat such infection.

The dosage administered of the penems of this invention is dependent upon a variety of factors, i e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g. transdermal.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose, and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols; hydrolyzed cereal solids; water; polyalkylene glycols; gums; and petrolatum; as well as other non-toxic compatible fillers, binders, disintegrants and lubricants commonly used in pharmaceutical formulations. Optionally, the compositions may also contain preservatives, aerosol propellants such as hydrocarbons, and coloring, thickening, suspending, dispensing, emulsifying, wetting, stabilizing and buffering agents. In addition, there may also be included in the composition other active ingredients to provide a broader spectrum of antibacterial activity and provide relief of concomitant symptoms such as inflammation.

The compounds of formula I may be prepared by the following reaction Scheme I:

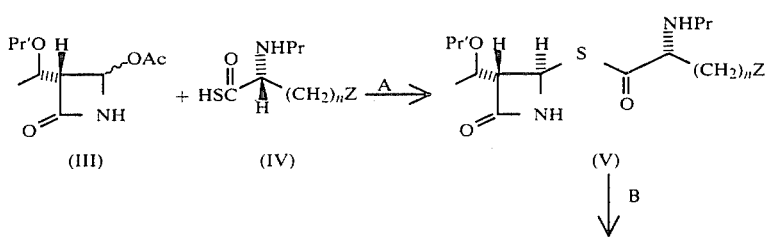

-continued

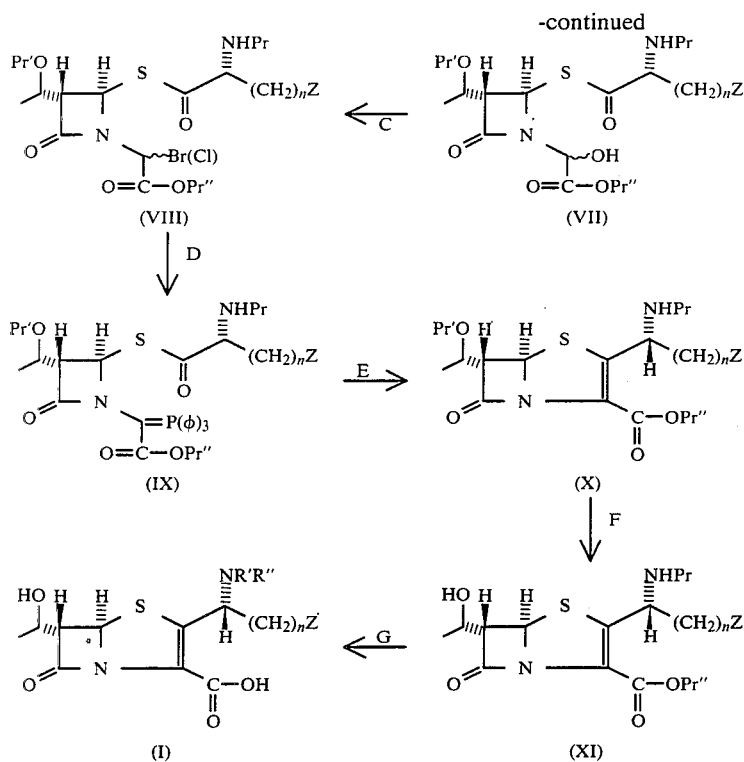

In Step IA, a 4-acetoxy-3-(protected-hydroxyethyl)azetidin-2-one of formula III wherein Pr' is a removable hydroxy protecting group is reacted with an alpha-(protected amino)-thiolcarboxylic acid of formula IV wherein Pr is a removable amino protecting group and n and Z are as hereinbefore defined except that any hydroxy, carboxy or amino group in the Z moiety is protected by a suitable removable protecting group so as to produce the intermediate of formula V wherein Pr, Pr', n and Z are as hereinbefore defined except that any hydroxy, carboxy or amino group in the Z moiety is protected by a suitable removable protecting group. Hydroxy-protecting groups Pr' are those known in the art such as t-butoxycarbonyl, 2,2,2,-trichloroethoxycarbonyl, 2-bromoethoxycarbonyl, or p-nitrobenzyloxycarbonyl, with 2,2,2-tricholorethoxycarbonyl being the general choice of use in the present invention. Typical amino-protecting groups Pr are those known in the art such as allyloxycarbonyl 2,2,2,-trichloroethoxycarbonyl, 2-bromoethoxy carbonyl, 4-methoxybenzyloxycarbonyl, t-butoxycarbonyl with the allyloxycarbonyl group being especially preferred for use in the present invention. This reaction is generally conduced in basic aqueous media, typically water to which sodium bicarbonate or sodium hydroxide has been added with the 4-acetoxy-3-protected-hydroxyethylazetidin-2-one of formula III being dissolved first in a water-miscible organic solvent such as tetrahydrofuran or dioxane. Generally, the reaction is conducted at temperatures of 0°–50° C., with room temperature being preferred, and for reaction times of 12–24 hours, depending upon the nature of the reactants and the temperature at which the reaction is conducted.

Where the Z moiety of a compound of formula IV is a hydroxy, carboxy or amino group, these groups must be protected prior to reaction with the 4-acetoxy-3-protected-hydroxyethylazetidin-2-one of formula III by suitable removable protecting groups. When this is the case, the preferred protecting groups utilized will be the same as, or at least removable under the same conditions as, the Pr and Pr' groups already utilized. Different or differently removable groups can be utilized, but this will add an additional removal step at the end of the reaction sequence.

Step IB of the reaction sequence involves the addition of a carboxy-protected 2-hydroxyacetic acid group to the nitrogen of the azetidinone intermediate of formula V to form the intermediate of formula VII. This reaction is accomplished by reacting the intermediate of formula V with a glyoxylic ester of the formula VIa or its hemiacetal of formula VIb

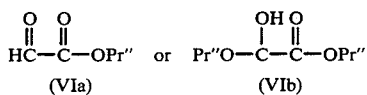

where Pr'' is a suitable readily removable protecting group. Any readily removable protecting group can be utilized, but preferably one is chosen which can be later removed under the same conditions as Pr and/or Pr'. For this reason the allyl group is particularly preferred since it can later be removed concurrently with the allyloxycarbonyl group utilized for the amino group of the compound of formula IV. Typically, this reaction is conducted in an organic solvent such as methylene chloride, chloroform or carbon tetrachloride and in the presence of a catalytic amount of an acid acceptor such as triethylamine or pyridine. Typical reaction times vary from about 5–60 minutes, with reaction temperatures being from about 0°–50° C., with room temperatures being generally preferred.

In Step IC of the reaction sequence, the hydroxy group of the intermediate of formula VII is replaced by a bromine or chlorine atom to afford the intermediate of formula VIII wherein Pr, Pr', Pr", n and R are as hereinbefore defined except that any hydroxy, carboxy or amino group in the Z moiety is suitably protected. This reaction is accomplished utilizing a halogenating agent such as thionyl chloride or thionyl bromide, a mesyl halide, such as mesyl chloride or bromide, or a phosphorus oxyhalide, especially the chloride, preferably in the presence of a basic (preferably organic) agent such as an aliphatic tertiary amine, for example, triethylamine, pyridine or collidine. Preferably, the reaction is carried out in the presence of a suitable solvent, such as methylene chloride, dioxane or tetrahydrofuran, at temperatures of from about −20° C. to 0° C.

Step ID of the reaction sequence involves the conversion of the halide intermediate of formula VIII into the phosphorane intermediate of formula IX wherein Pr, Pr', Pr", n and Z are as hereinbefore defined except that any hydroxy, carboxy or amino group in the Z moiety is suitably protected. This conversion is accomplished by reaction of the intermediate of formula VIII with a suitable phosphine compound such as a tri-loweralkyl-phospine, for example tri-n-butylphosphine, or a triarylphosphine, for example, triphenylphosphine. Triphenylphosphine is generally preferred for use in the present invention. The reaction is preferably carried out in the presence of a suitable inert solvent such as dioxane, tetrahydrofuran or dimethylformamide. Depending upon the reactivity, the reaction is conducted with cooling or at elevated temperatures, preferably at about room temperature.

In Step IE of the reaction sequence, the phosphorane intermediate of formula IX is cyclized to afford the penem intermediate of formula X wherein Pr, Pr', Pr", n and Z are as hereinbefore defined except that any hydroxy or carboxy group in the Z moiety is suitably protected. This reaction is accomplished by dissolving the phosphorane intermediate of formula IX in a suitable organic solvent such as benzene, toluene or xylene and heating to reflux temperature for a period of 24–48 hours.

Steps IF and IG involve the removal of the protecting groups Pr, Pr' and Pr" and any protecting groups in the Z moiety. The reaction conditions for deprotection depend on the nature of the protecting groups utilized. For instance, the 2,2,2-trichloroethoxycarbonyl group is preferably removed by treatment with zinc and glacial acetic acid at temperatures of from about −30° to about 0° C. Groups such as p-nitrobenzyloxycarbonyl are removed by hydrogenolysis, for example by treating with hydrogen in the presence of a noble metal catalyst such as palladium. The allyl and allyloxycarbonyl groups, preferred groups for use in the present invention, are most preferably removed utilizing the methods taught in U.S. Pat. No. 4,314,942 to McCombie (1982) which utilize 2-ethylhexanoic acid or an alkali metal salt thereof and a catalytic amount of an organic soluble palladium complex to effect removal of the protecting groups and afford the desired compound of formula I. Additionally, these protecting groups may be removed by the method of Tsuji, taught in Tetrahedron Letters, 7, 613 (1979).

Salts and metabolizable esters of the compounds of formulae Ia and Ib may be produced by methods well-known in the beta-lactam art. For example, salts of such compounds with acid groups can be formed, for example, by treating with metal compounds such as alkali metal salts of suitable carboxylic acids, or with ammonia or a suitable organic amine, wherein preferably stoichiometric amounts or only a small-excess of the salt-forming agent used. Acid addition salts of the compounds of formulae Ia and Ib with basic groupings are obtained in the usual manner, for example, by treating with an acid or a suitable anion exchange reagent. Inner salts of the compounds of formula, i.e., a zwitterion, may be formed by neutralizing salts such as acid addition salts to the isoelectric point. The metabolizable esters are preparable in a manner analogous to the preparation of the corresponding esters of penicillins and cephalosporins.

Salts may be convented in the usual manner into the free carboxy compounds.

Resulting mixtures of isomers can be separated into the individual isomers according to known methods. Diastereomeric mixtures, for example, can be separated by fractional crystallization, absorption chromatography (column or thin layer) or other suitable separation methods. Resulting racemates can be resolved into the antipodes in the customary manner, for example, by forming a mixture of diastereomeric salts with optically active salt-forming reagents, separating the diastereomeric salts and converting the salts into the free compounds, or by fractional crystallization from optically active solvents.

The starting materials of formula III may be produced by methods known in the art, i.e., according to the methods taught by European patent application No. 80810004, published July 23, 1980 or by British Published application No. 2013674 (1979).

The starting materials of formula IV are produced by first protecting the amino group of an alpha-aminocarboxylic acid of the formula XII

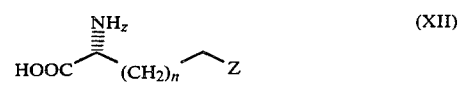

wherein n is as herebefore defined, to afford the intermediate of the formula XIII,

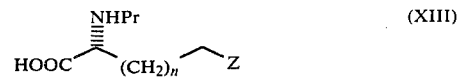

where Pr is a suitable readily removable amino protecting group and n and Z are as hereinbefore defined except that where the Z moiety contains a hydroxy, carboxy or amino group, that group is also suitably protected at this stage. Suitable protecting groups are those typically utilized in the beta-lactam art, such as p-nitrobehzyl oxycarbonyl and allyloxycarbonyl. For the purposes of this invention, the allyloxycarbonyl group is a particularly preferred protecting group. Typically, this reaction is conducted in aqueous media to which a suitable inorganic base, such as sodium hydroxide has been added. The protecting group is added via a reactive derivative, such as the chloroformate. Preferably any protecting group utilized for the Z substituent is the same as either the amino protecting group or the 3-hydroxy protecting group of the starting material of formula III but this need not necessarily be the case.

The carboxy group of the compound of formula XIII is then converted to a thiolcarboxy group, thus affording the starting material of formula IV. This conversion is typically accomplished by dissolving the compound of formula XIII in a suitable solvent, such as tetrahydrofuran or dioxane, and treating it with isobutylchloroformate and an organic acid acceptor such as triethylamine or pyridine, followed by the addition of hydrogen sulfide gas. Typically, the reaction is conducted at temperatures of about −20° to about 0° C. with reaction time of 5–30 minutes being generally sufficient.

Compounds of formula I may also be prepared from racemic starting materials of formula IV (i.e., substitute D,L mistures for compounds of formula XII). The desired 1'R isomer may be separated from the mixture using conventional techniques as described above.

An alternate method for the preparation of the compounds of formula I involves the reaction of a mixed anhydride of formula XIV

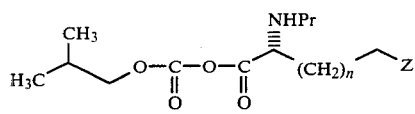
(XIV)

wherein Pr, n and Z are as hereinbefore defined except that any hydroxy, carboxy or amino group in the Z moiety is suitably protected, with a silver salt of the formula XV

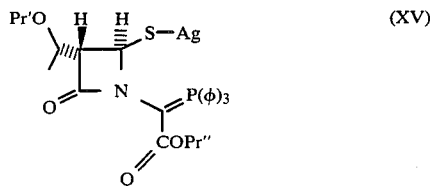
(XV)

wherein Pr' and Pr'' are as hereinbefore defined to afford the intermediate of formula IX which is then subjected to the same steps as hereinabove described to give the compounds of formula I. This reaction is typically conducted in an inert solvent such as tetrahydrofuran or ethyl ether at temperatures of from about −20° to about 0° C. Reaction times vary from about 0.5 to 2 hours.

Preferably the compound of formula XIV is prepared in situ in the reaction media by contacting a compound of formula XIII with a chloroformate agent, such as isobutyl chloroformate, and an acid acceptor, such as pyridine or triethylamine. The resultant compound of formula XIV is then immediately reacted with the silver salt of formula XV.

The silver salt of formula XV is prepared by the following reaction Scheme II:

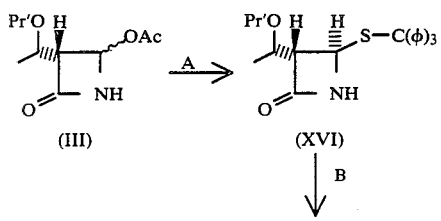

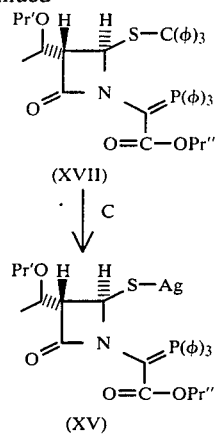

Step II A of this reaction Scheme involves the conversion of the starting material of formula III to a 2-triphenylmethyl thio azetidinone intermediate of the formula XVI wherein Pr' is as hereinbefore defined. This is accomplished by reacting the compound of formula III with triphenylmethylthiol in the presence of an acid acceptor. Either an inorganic, such as potassium or sodium carbonate, or organic, such as triethylamine, acid acceptor can be utilized. Typically, the reaction is conducted at temperatures of 0°–50° C. with room temperatures being preferred. Preferably, an organic solvent such as acetonitrile or pyridine is utilized. Reaction times typically vary from about 2–24 hours, depending upon the other reaction conditions utilized.

In Step II B of this reaction scheme, the intermediate of formula XVI is converted to the phosphorane intermediate of formula XVII. This is accomplished in a manner essentially as described above for the conversion of the intermediate of formula V to the intermediate of formula IX, utilized similar, if not identical, reaction conditions and reagents.

The final step, Step III C, involves the conversions of the intermediate of formula XVII to the silver salt intermediate of formula XV. Typically, this reaction is conducted in a suitable organic solvent such as a halogenated hydrocarbon such as methylene chloride. The silver reagent is generally a salt such as silver nitrate. Any salt which forms a soluble salt in the selected solvent can be utilized. An organic or inorganic base, such as aniline, pyridine, collidine or an alkali metal carbonate is added to the reaction mixture. Preferably, the temperature range is from about −20° to about 25° C. Reaction times vary, depending upon the particular conditions and reagents employed, but are generally less than ½ hour.

The following preparations and examples describe in detail compounds and compositions illustrative of the present invention and methods which have been devised for their preparation. It will be apparent to those skilled in the art that many modifications, both of materials and methods, may be practiced without departing from the purpose and intent of this disclosure. Throughout these examples and preparations, "IR" denotes infrared spectra, "NMR" denotes nuclear magnetic resonance spectra and $[\alpha]_D$ denotes optical rotation.

PREPARATION A

A. N-allyloxycarbonyl-D-methionine

To a solution of 15.00 g D-methionine in 25.2 ml 4N sodium hydroxide cooled to about 0° C. is added, with stirring, 15.60 ml allyl chloroformate and 41.49 ml 4N sodium hydroxide. After the addition is completed, the reaction is stirred for an additional ten minutes at 0° C. and then allowed to warm to room temperature for an additional 20 minutes. The reaction mixture is then washed twice with ethyl ether. The aqueous layers are separated, acidified to pH2 with concentrated hydrochloric acid and then refrigerated for one hour. The cooled solution is then extracted three times with 100 ml portions of ethyl ether. The ether extracts are combined, dried over anhydrous sodium sulfate and the solvents removed under vacuum to afford the title product having $[\alpha]_D^{26} = -6.5°$ (CHCl$_3$, c.=0.4);
Mass spectra: M+, 233; NMR: $\delta$(CDCl$_3$) 2.13 ppm (s,3H), 2.58 ppm (t, 2H).

B. N-allyloxycarbonyl-D-2-amino-4-methylthiothiolbutyric acid

To a solution of 10 g N-allyloxycarbonyl-D-methionine (prepared as in paragraph A of this example) in 100 ml tetrahydrofuran and 7 ml pyridine cooled to about $-15°$ C. is added a solution of 6.6 ml isobutylchloroformate in 10 ml tetrahydrofuran over a period of ten minutes. The resulting suspension is stirred at about $-15°$ to $-10°$ C. for one-half hour. Hydrogen sulfide gas is then bubbled through the reaction mixture for fifteen minutes at about $-10°$ C. The reaction mixture is allowed to warm to room temperature until the evolution of carbon dioxide ceases and then is diluted with 100 ml water. The solution is acidified with 25 ml 2N hydrochloric acid and then extracted twice with 80 ml portions of ethyl acetate. The extracts are combined, washed twice with 100 ml portions of water, six times with 50 ml portions of water, once with brine, and then dried over sodium sulfate. The solvent is removed by evaporation to afford the title compound having Mass spectra: M+ =249.

Preparation B

Utilizing the procedure described in paragraph A of Preparation A and the appropriate amino acid, there are produced the following intermediate used in this invention:

N-Allyloxycarbonyl-S-Methyl-D-cysteine;
N-Allyloxycarbonyl-D-alanine;
N-Allyloxycarbonyl-D-serine;
N-Allyloxycarbonyl-D-homoserine;
N-Allyloxycarbonyl-D-histidine;
bis,N,N-Allyloxycarbonyl-D-lysine;
N-Allyloxycarbonyl-D-tyrosine;
N-Allyloxycarbonyl-D-phenylalanine;
N-Allyloxycarbonyl-D-tryptophan;

PREPARATION C

The protected amino acids of Preparation A are converted to the corresponding thioacids using the procedure of paragraph B of Preparation A to afford the following:

N-allyloxycarbonyl-D-2-amino-3-methylthiothiolpropionic acid;
N-allyloxycarbonyl-D-2-amino-thiolpropionic acid;
N-allyloxycarbonyl-D-2-amino-3-hydroxythiolpropionic acid;
N-allyloxycarbonyl-D-2-amino-4-hydroxythiolbutyric acid;
N-allyloxycarbonyl-D-2-amino-3-(4-imidazole)thiolpropionic acid;
bis-N,N-allyloxycarbonyl-D-2,6-diaminothiolcaproic acid;
N-allyloxycarbonyl-D-2-amino-3-p-hydroxyphenylthiolpropionic acid;
N-allyloxycarbonyl-D-2-amino-3-phenylthiolpropionic acid;
N-allyloxycarbonyl-D-2-amino-3-indolethiolpropionic acid; and

PREPARATION D

A. N-Allyloxycarbonyl-D-glutamic acid $\gamma$-allyl ester

A solution D-glutamic acid (6.0 g) in water (30 ml) and ethanol (10 ml) is stirred with copper carbonate (3.6 g) for 1 hour. To this mixture is then added potassium bicarbonate (5.28 g) and allyl bromide (4.5 ml) and the mixture is stirred overnight at room temperature. Excess hydrogen sulfide is bubbled through the mixture, which is then filtered and the filtrate stirred vigorously with potassium bicarbonate (5.8 g) and allyl chloroformate (5.4 ml) for 1 hour. The reaction is then washed with ethyl ether and the aqueous phase is acidified with dilute mineral acid and extracted with ethyl acetate. The extract is dried and evaporated. The residual oil is purified by chromatography on silica gel (100 g). Elution with chloroform:methanol:ammonia (7:1:0.2) affords the title compound having $[\alpha]_D^{26} = +3.2°$ (c.=4.8, chloroform)

B. N-Allyloxycarbonyl-D-glutamic $\alpha$-thiolacid $\gamma$-allyl ester

The protected glutamic acid of paragraph A is converted to the title compound using the procedure of paragraph B of Preparation A.

PREPARATION E (3S,4R,5R)-4-Acetoxy-3-(1-trichloroethoxycarbonyloxyethyl)azetidin-2-one A. To a solution of 100 g 6-$\beta$-aminopenicillanic acid in 1200 ml 2.5N sulfuric acid is added 150 g sodium bromide. To the stirred solution at 0° C. is added simultaneously 40 g sodium nitrite in 150 ml water and 40 ml bromine. The addition is completed in 10 minutes, maintaining the temperature at 0° to 5° C. The mixture is then stirred rapidly for 1 hour, then filtered. The filter cake is washed with water and taken up to 600 ml ethyl acetate. The ethyl acetate solution is washed with water, cold dilute sodium bisulfite solution and then again with water. After drying over anhydrous sodium sulphate, the solvent is removed under vacuum to afford 67 g in 85:15 ratio (by NMR data) of 6,6-dibromopenicillanic acid and 6$\alpha$-bromopenicillanic acid having:

IR: 1728 cm$^{-1}$ and 1800 cm$^{-1}$ (chloroform solution); NMR: $\delta$=5.7, (1H,s); 4.5, (1H,s); 1.55–1.67, (6H).

B. To a solution of 67 g in 85:15 ratio of 6,6-dibromopenicillanic acid to 6$\alpha$-dibromopenicillanic acid in 500 ml of dimethylformamide at 0° C. is added 37.3 g finely powdered potassium carbonate. The solution is stirred 5–10 minutes and 38.3 g methyl iodide is added. The reaction mixture is then stirred for 2 hours allowing the temperature to come to ambient. The reaction is followed by thin layer chromatography eluting with methylene chloride. When complete, the reaction is decanted and the solvent removed under high vacuum to leave 100 ml of solution. To this is added 600 ml ethyl acetate. The solution is then washed with water, dried over anhydrous sodium sulphate and concentrated under vacuum to afford 63 g crude methyl ester. Subsequently, 48 g of pure methyl 6,6-dibromopenicillanate is isolated from this crude product by high pressure liquid chromatography eluting with methylene chloride. This compound exhibits the following characteristics:

NMR: $\delta = 5.7$, (1H, s); 4.48, (1H, s); 3.73, (3H, s); 1.42, (3H, s); 1.59, (3H, s).

C. To a solution of 13.7 g methyl 6,6-dibromopenicillanate in 250 ml dry tetrahydrofuran at $-78°$ C. under nitrogen is added 14.7 ml of 3M methyl magnesium bromide in ethyl ether. After stirring for 30 minutes at $-78°$ C., 8 g of freshly distilled acetaldehyde is added and stirring continued for 45 minutes. The reaction mixture is warmed to $-20°$ C. at which time 50 ml 1M potassium phosphate monobasic is added and stirring continued for 5 minutes. The reaction mixture is then poured into 1 liter cold ethyl acetate and washed once with 150 ml brine solution and twice with 150 ml water. The ethyl acetate layer is separated, dried over anhydrous sodium sulfate and evaporated under vacuum. The products, methyl 6α-bromo-6β-(1-hydroxyethyl)-penicillanate and methyl 6β-bromo-6α-(1-hydroxyethyl)penicillanate, are detected by thin layer chromatography eluting with 10% ethyl acetate/chloroform.

D. To a solution of 8.0 g methyl 6-bromo-(1-hydroxyethyl)penicillanate in 200 ml 95% ethanol is added 800 mg 10% palladium on calcium carbonate. The solution is shaken under 2 atmospheres hydrogen pressure for 5 hours. Disappearance of starting material is followed by thin layer chromatography eluting with 20% ethyl acetate/chloroform. The catalyst is filtered and 100 ml 1M potassium phosphate buffer at pH 7 is added. The precipitate formed is filtered and washed with ethanol. The ethanol is removed under vacuum and 200 ml ethyl acetate added. After washing twice with 50 ml water, and drying over anhydrous sodium sulfate, the ethyl acetate is removed under vacuum to afford a crude mixture of methyl 6-(1-hydroxyethyl)penicillanate. Column chromatography of 18 g of said mixture eluting with 20% ethyl acetate affords 6.4 g methyl (5R,6S,8R)-6-(1-hydroxyethyl)-penicillanate having the following spectra:

NMR: $\delta = 2.4–2.7$, (1H, d); 4.41, (1H, s); 3.74, (3H, s); 3.2–3.33, (1H); 1.25–1.35, (3H, d); 1.44, (3H, s); 1.61, (3H, s).

E. To a solution of 6.2 g methyl (5R,6S,8R)-6-(1-hydroxyethyl)penicillanate in 60 ml. dry methylene chloride at 0° C. under nitrogen is added 3.8 ml pyridine then 3.3 ml β, β, β-trichloroethylchloroformate. The reaction is stirred 15 minutes until all starting material is reacted (as determined by thin layer chromatography with 20% ethyl acetate/chloroform). The solution is poured into 250 ml cold methylene chloride and washed twice with cold 10% phosphoric acid solution, once with cold dilute sodium bicarbonate, and then with water. After drying over anhydrous sodium sulfate, the solvent is removed under vacuum to afford 10.0 g methyl (5R,6S,8R)-6-(1-trichloroethoxycarbonyloxyethyl)penicillanate having the following spectra:

NMR: $\delta = 5.13–5.16$, (1H, d); 4.78, (2H, s); 4.43, (1H, s); 3.76, (3H, s); 3.38–3.58, (1H); 1.45–1.63, (9H).

F. To a solution of mercuric acetate (73.35 g) in glacial acetic acid (500 ml) at 80° C. is added methyl (5R,6S,8R)-6-(1-trichloroethoxycarbonyloxyethyl)-penicillinate (50 g) in small lots. After 2 hours, the mixture is filtered, diluted with ethyl acetate (2 L), washed successively with water, 10% sodium bicarbonate solution, and brine and is then dried and evaporated. The resulting (3S,4R,5R)-1-[(2-methyl-1-methoxycarbonyl)-prop-1-enyl]-3-(1-trichloroethoxycarbonyloxyethyl)-4-acetoxyazetidin-2-one is dissolved in acetone (860 ml) and water (70 ml). The solution is stirred and cooled in ice bath while adding potassium permanganate (23 g). After ½ hour, the solution is diluted with ethylacetate (500 ml) filtered through celite, concentrated to 300 ml, diluted with an equal volume of ethylacetate and washed several times with water. The organic layer is dried and evaporated to afford the title compound having the following spectra:

NMR: $\delta 1.42$ (d, J=6 cps); 1.55 (d, J=6 cps); 3.4 (dd, J=2,8 cps); 4.76 (s), 5.86 (d, J=1.5 cps); 5.90 (d, J=3.0 cps).

PREPARATION F (3R,4S,5R)-Silver-3-(1'-trichloroethoxycarbonyloxy-1'-ethyl)-1-(allyl-2''-triphenylphosphoranylidene-2''-acetate)-2-azetidinone-4-thiolate A. A solution of the title compound of Preparation D (50 g) in acetonitrile (750 ml) is stirred overnight with potassium carbonate (39.6 g) and triphenylmercaptan (59.8 g) under argon. The mixture is filtered, and the filtrate is evaporated to dryness. The resulting crude product is chromatographed on silica gel (540 g). Elution with 10% ethylacetate:hexane affords (3S,4R,5R)-3-(1'-trichloroethoxycarbonyloxyethyl)-4-tritylthio-azetidin-2-one.

B. The product from Step A (55.9 g) in methylene chloride (600 ml) is treated with allyl glyoxylate allyl hemiacetal (17 g) and triethylamine (1.0 g). After stirring for 1 hour the solution is cooled in ice bath, followed by addition of mesyl bromide (62.96 g) in one lot and then dropwise addition of a solution of triethylamine (40 g) in methylene chloride (90 ml) while maintaining the reaction temperature below 2° C. After 1 hour, the reaction mixture is filtered through silica gel (300 g) and the elution with 5% ethylacetate:methylene chloride are collected and evaporated. The resulting bromo intermediate is dissolved in dimethylformamide (300 ml). Triphenylphosphine (30 g) is added and the reaction is stirred for 15 hours at room temperature under argon blanket. The solution is diluted with ethylacetate (500 ml), washed with 10% aqueous sodium bicarbonate, brine, dried over sodium sulfate and evaporated under reduced pressure. The resulting crude product is chromatographed on silica gel (1.5 kg). Elution with 20% ethylacetate:hexane affords (3S,4R,5R)-3-(1'-trichloroethoxycarbonyloxyethyl)-1-(allyl-2''-triphenylphosphoranylidene-2''-acetate)-4-tritylthio-2-azetidinone.

C. To a mixture of 5.73 g (3S,4R,5R)-3-(1'-trichloroethoxycarbonyloxyethyl)-1-(allyl-2''-triphenylphosphoranylidene-2''-acetate)-4-tritylthio-2-azetidine in 57 ml methanol is added sufficient methylene chloride to cause solution. The solution is then cooled to 0° C. and 0.92 ml pyridine is added followed by the dropwise addition over a 10 minute period of a solution of 1.37 g silver nitrate in 8 ml water. After five minutes, the reaction mixture is poured over 100 ml ice water. The methylene chloride layer is then separated and the remaining water layer is extracted twice with 50 ml portions of ethyl acetate. The methylene chloride layer and ethyl acetate layers are combined, washed five times with 100 ml portions of cold water and then evaporated to give the title compound.

EXAMPLE 1

Method A

A.

(3S,4R,5R,2'R)-3-(1-trichloroethoxycarbonyloxethyl)-4-[2'-allyloxycarbonylamino-4'-methylthiobutyroyl)thio]-2- azetidinone N-allyloxycarbonyl-D-2-amino-4-methylthiothiolbutyric acid (prepared as described in Preparation A of the specification) is dissolved in 20 ml water and 3.6 g sodium bicarbonate. To this is added 13.4 g of 4-acetoxy-3-(1-trichloroethoxycarbonyloxyethyl)azetidin-2-one (prepared as described in Preparation B of this specification) dissolved in 100 ml tetrahydrofuran and the resulting solution is stirred for 16 hours. The reaction mixture is then diluted with 100 ml portions of ethyl acetate. The extracts are combined, washed three times with 100 ml portions of water and dried over sodium sulfate evaporation of the solvents affords a residue which is purified by chromatography on 300 g silica gel to afford the title compound having $[\alpha]_D^{26} = +76.2°$ (c. = 0.6 CHCl$_3$);

Mass spectra, M+ = 538; and

NMR: $\delta$ = 1.45 (d,J = 7 cps); 2.08; 2.5 (m); 3.38 (dd,J = 2,7 cps); 5.25 (d, J = 2 cps).

B.

(3S,4R,5R,2'R)-1-(1''-allyloxycarbonyl-1''-hydroxymethyl)-3-(1-trichloroethoxycarbonyloxyethyl)-4-[(2'-allyloxycarbonylamino-4'-methylthiobutylroyl)thio]-2-azetidinone To a solution of 20 g of (3S,4R,5R,2'R)-3-(1-trichloroethoxycarbonyloxyethyl)-4-[2'-allyloxycarbonylamino-4'-methylthiobutylroyl)thio]-2-azetidinone (prepared as in paragraph A of this example) and 5.39 g 2-allyloxy-2-hydroxyacetic acid allyl ester in 100 ml methylene chloride is added 0.0513 ml triethylamine in 1 ml methylene chloride. The resulting solution is stirred for fifteen minutes, whereupon thin layer chromatography indicates formation of the title product.

C.

(3S,4R,5R,2'R)-1-(1''-allyloxycarbonyl-1''-bromomethyl)-3-(1-trichloroethoxycarbonyloxyethyl)-4-[2'-allyloxycarbonylamino-4'-methylthiobutyroyl)thio]2-azetidinone A solution of (3S,4R,5R,2'R)-1-(1''-allyloxycarbonyl-1''-hydroxymethyl)-3-(1-trichloroethoxycarbonyloxyethyl)-4-[2'-allyloxycarbonylamino-4'-methylthiobutyroyl)thio]-2-azetidinone in methylene chloride (prepared as in paragraph B of this example) is cooled to about −10° C. To this is added 5.9 g mesyl bromide in one portion with stirring. Then a solution of 5.13 ml triethylamine in 10 ml methylene chloride is added dropwise over a period of about ten minutes. The reaction mixture is chromatographed on silica gel using 5:95 ethylacetate:methylene chloride to afford the title product.

D.

Allyl-(3S,4R,5R,2'R)-3-(1-trichloroethoxycarbonyloxyethyl)-4-[2'-allyloxycarbonylamino-4'-methylthiobutyroyl)thio]-2-azetidinon-1-yl-2''-triphenylphosphoranyl-2''-acetate To a solution of (3S,4R,5R,2'R)-1-(1''-allyloxycarbonyl-1''-bromomethyl)-3-(1-trichloroethoxycarbonyloxyethyl)-4-[2'-allyloxycarbonylamino-4'-methylthiobutyroyl)thio]-2-azetidinone (prepared as described in paragraph C of this example) in 100 ml dimethylformamide under a nitrogen atmosphere is added 14.5 g triphenylphosphine. After stirring until homogeneous, the solution is allowed to stand at room temperature for about 19 hours. The reaction mixture is diluted with 100 ml water and extracted twice with 200 ml portions of ethyl acetate. The extracts are combined, washed six times with 50 ml portions of water and then once with brine. Evaporation of the solvents affords a residue which is chromatoorphed on 200 g silica gel, using 10:90 ethyl acetate:methylene chloride as eluant, to give the title compound as a colorless solid having $[\alpha]_D^{26} = +22.6°$ (c. = 0.3, CHCl$_3$); and NMR: $\delta$ = 4.22 (dd,J = 2,8 cps); 5.61 (d,J = 2 cps).

E.

Allyl-(5R,6S,8R,1'R)-6-(1-trichloroethoxycarbonyloxyethyl)-2-[N-allyloxycarbonyl-(1'-amino-3'-methylthio)propyl]-2-penem-3-carboxylate A solution of 16 g of allyl-(3S,4R,5R,2'R)-3-(1-trichloroethoxycarbonyloxyethyl)-4-[(2'-allyloxycarbonylamino-4'-methylthiobutyroyl)thio]-2-azetidinone-1-yl-2''-triphenylphosphoranyl-2''-acetate (prepared as described in Paragraph D of this example) in 1.8 liters benzene under a nitrogen atmosphere is refluxed for 34 hours. Then, the solvent is removed by evaporation, and the residue applied as a benzene solution to a 150 g silica gel column. Chromatography using 20:80 ethyl acetate:petroleum ether (30°–60°) as eluant affords the title compound having $[\alpha]_D^{26} = +84.1°$ (c. = 0.3, CHCl$_3$);

NMR: $\delta$ = 1.54 (d,J = 7 cps), 2.15 (s); 2.59 (m); 3.97 (dd,J = 1.5, 7 cps); 4.85 (s); 5.67 (d,J = 1.5 cps).

F.

Allyl-(5R,6S,8R,1'R)-6-(1-hydroxyethyl)-2-[N-allyloxycarbonyl-(1'-amino-3'-methylthio)propyl]-2-penem-3-carboxylate A solution of allyl-(5R,6S,8R,1'R)-6-(1-trichloroethoxycarbonyloxyethyl)-2-[N-allyloxycarbonyl-(1'-amino-3'-methylthio)propyl]-2-penem-3-carboxylate (prepared as described in paragraph E of this example) in 4 ml tetrahydrofuran is cooled to about −15° to −20° C. Then, 1.2 ml glacial acetic acid and 1.2 ml water is added, followed by 0.4 g zinc in portions over a 3½ hour period. When the reaction proceeds no further, 20 ml ethyl acetate is added and the mixture is filtered. The zinc residue is washed three times with 20 ml portions of ethyl acetate. These washings are added to the filtrate and the solution is then washed successively with two 50 ml portions brine, one 75 ml portion 10% NaHCO$_3$ and two 50 ml portions brine. After drying over anhydrous sodium sulfate, the solvents are removed and the residue chromatographed on 7.6 g silica gel. Elution first with 15:85 hexane/chloroform and then chloroform affords the title product as a white solid having $[\alpha]_D^{26} = +71.9°$, (c.=03, CHCl$_3$);

Mass spectra: M+ = 442;

NMR: $\delta = 1.34$ (d,J=7 cps); 2.13 (s); 2.56 (m); 3.73 (dd,J =1.5, 7 cps); 5.57 (d,J=1.5 cps).

G.
(5R,6S,8R,1'R)-6-(1-hydroxyethyl)-2-[(1'-amino-3'-thiomethyl)propyl]-2-penem-3-carboxylic acid To a solution of 0.19 g of allyl-(5R,6S,8R,1'R)-6-(1-hydroxyethyl)-2-[N-allyloxycarbonyl-(1'-aminomethylthio)propyl]-2-penem-3-carboxylate (prepared as in paragraph F of this example) in 1.9 ml ethyl acetate under nitrogen at room temperature is added 0.12 g triphenylphosphine, 0.072 g tetrakis (triphenylphosphine) palladium-(0) and 0.94 ml of 1.0M 2-ethylhexanoic acid (in methylene chloride). After stirring one hour, the solvent is removed and the residue diluted with 10 ml water and 10 ml chloroform. The aqueous layer is separated, washed ten times with chloroform. The residual chloroform is then removed to give the title product having $[\alpha]_D^{26} = 57.5°$, (c.=0.3, H$_2$O);

IR: 5.65$\mu$;

NMR: $\delta = 1.3$ (d,J=7 cps); 2.13 (s); 2.68 (m); 3.97 (dd,J=1.5, 7 cps); 5.76 (d,J=1.5 cps).

Method B

A. Allyl (3S,4R,5R,2'R)-3-(1-trichloroethoxycarbonyloxyethyl)-4-[2'-allyloxycarbonylamino-4'-methylthiobutyroylthio]-2-azetidin-1-yl-2''-triphenylphosphoranyl-2''-acetate To a solution of N-allyloxycarbonyl-D-methionine (prepared as in paragraph A of preparation A of this specification) in 9 ml of freshly distilled tetrahydrofuran cooled to about $-15°$ C. and maintained under a nitrogen atmosphere is added 0.64 ml pyridine and 0.31 ml methyl chloroformate in 0.5 ml tetrahydrofuran. To the resultant N-allyloxycarbonyl-D-methionine mixed anhydride is added dropwise over a ten minute period 2.08 of the (3S,4R,5R)-silver-3-(1'-trichloroethoxycarbonyloxyethyl)-1-(allyl-2''-triphenylphosphoranylidine-2''-acetate)-2-azetidinone-4-thiolate (prepared as in Preparation E of this specification). The mixture is stirred for 1¼ hour at about $-15°$ to $-10°$ C., filtered and then diluted with 100 ml ethyl acetate. The mixture is washed twice with 10% NaHCO$_3$, four times with 100 ml portions of water and dried over anhydrous sodium sulfate. The solvents are removed by evaporation to give a residue which is then chromatographed on 40 g silica gel. Elution with 30:70 ethyl acetate:hexane affords the title compound as a white, puffy solid.

B.
(5R,6S,8R,1'R)-6-(1-hydroxyethyl)-2-[1'-amino-3'-thiomethyl)propyl]-2-penem-3-carboxylic acid Repetition of the procedures detailed in Paragraphs E to G of Method A of Example 1 affords the title compound.

EXAMPLE 2

A.
Allyl-(5R,6S,8R,1'R)-6-(1-trichloroethoxycarbonyloxyethyl)-2-[N-allyloxycarbonyl(1'-aminoethyl)]2-penem-3-carboxylate The title compound is obtained from N-allyloxycarbonyl-D-alanine (Preparation B) or from N-allyloxycarbonyl-D-2-aminothiolpropionic acid (Preparation C) using the procedures described in Example 2, Step A, and has IR: 5.69$\mu$;

NMR: $\delta = 1.05$ (d,J=8 cps); 1.65 (d,J=6 cps); 3.7 (dd,J=6,2 cps); 5.51 (d,J=2 cps).

B.
(5R,6S,8R,1'R)-6-(1-hydroxyethyl)-2-(1'-aminoethyl-2-penem-3-carboxylic acid The compound of Step A of this examples is deprotected using the procedures described in Step F and G of Example 1 to afford the title compound having:

$[\alpha]_D^{26} = +61.1°$ (c.=2;8, H$_2$O);

IR: 5.62$\mu$;

NMR: $\delta = 1.27$ (d,J=6 cps); 1.52 (d,J=7 cps); 3.92 (dd,J=1.6,6 cps); 5.67 (d,J=1.6 cps).

EXAMPLE 3

A.
Allyl-(5R,6S,8R,1'R)-6-(1-trichloroethoxycarbonyloxyethyl)-2-[N-allyloxycarbonyl(1'-amino-3-carboallyloxy)propyl]-2-penem-3-carboxylate The title compound is obtained from N-allyloxycarbonyl-D-glutamic acid $\gamma$-allyl ester (Preparation D, Step A) or from N-allyloxycarbonyl-D-glutamic-$\alpha$-thiolacid-$\gamma$-allyl ester (Preparation D, Step B) using the procedures described in Example 1, and has:

IR: 5.58, 5.68, 5.82, 6.3$\mu$;

$[\alpha]_D = +59.6$ (c=2.5, CHCl$_3$);

Mass Spectra: 654 (M+);

NMR: $\delta 1.45$ (d,J=7); 3.90 (dd,J=7,2 cps); 4.71 (s); 5.54 (d,J=2 cps).

B.
(5R,6S,8R,1'R)-6-(1-hydroxyethyl)-2-[(1'-amino-3-carboxy)propyl]-2-penem-3-carboxylic acid The compound of Step A of this example is deprotected using the procedures described in Steps F and G of Example 1 to afford the title compound having:

IR: 5.64$\mu$, 6.3$\mu$;

$[\alpha]_D = +67.5°$ (c=1.6, H$_2$O);

NMR: $\delta 1.27$ (d,J=7 cps); 3.92 (dd,J=7, 1.9 cps); 5.71 (d,J=1.9 cps).

EXAMPLE 4

A.
Allyl-(5R,6S,8R,1'R)-6-(1-trichloroethoxycarbonyloxyethyl)-2-[N-allyloxycarbonyl-(1'-amino-2'-methylthio)ethyl]-2-penem-3-carboxylate The title compound is obtained from N-allyloxycarbonyl-S-methyl-D-cysteine (Preparation B) or from N-allyloxycarbonyl-D-2-amino-3-methylthiothiolpropionic acid (Preparation C) using the procedures described in Methods A or B, respectively, of Example 1, and has IR: 5.65$\mu$;

$[\alpha]_D = +68.3°$ (c=0.4, CHCl$_3$);

NMR: $\delta = 1.5$ (d,J=7 cps); 2.16 (s); 3.95 (dd,J=7,2 cps); 4.75 (s); 5.65 (d,J=2 cps).

B.
(5R,6S,8R,1'R)-6-(1-hydroxyethyl)-2-[(1'-amino-2'-methylthio)ethyl]-2-penem-3-carboxylic acid The compound of Step A of this examples is deprotected using the procedures described in Steps F and G of Example 1 to afford the title compound having:
IR: 5.68μ;
[α]$_D$ = +7.2° (c=0.25, H$_2$O);
NMR: δ=1.35 (d,J=6.5 cps); 2.2 (s); 3.1 (d,J=7 cps); 4.0 (dd,J=5, 1.8 cps); 5.8 (d,J=1.8 cps);

EXAMPLE 5
(5R,6S,8R,1'R)-6-(1-Hydroxyethyl)-2-[N-acetimidoyl-(1'-amino-3'-methylthio)propyl]-2-penem-3-carboxylate, sodium salt A solution of (5R,6S,8R,1'R)-6-(1-hydroxyethyl)-2-[(1'-amino-3'-methylthio)propyl]-2-penem-3-carboxylic acid (0.3 g) from Example 1 in 0.5M sodium 2-ethylhexanoate solution in water (2 ml) is treated with ethylacetimidate (0.5 g) at 20° C. The solution is stirred for 30 minutes and then chromatographed on Dowex 50×4, eluted with water and the fractions containing the title compound and lyophilized to give the title compound having: IR: 5.68μ.

EXAMPLE 6
(5R,6S,8R,1'R)-6-(1'hydroxyethyl)-2-[1'-guanidoyl-3'-methylthio)propyl]-2-penem-3-carboxylate, sodium salt A solution of the product from Example 1 (0.3 g) in aqueous 0.5M sodium 2-ethylhexanoate (4 ml) is treated with S-benzyl thiourea hydrochloride (0.3 g) for 1 hour. The title compound is isolated by reverse phase HPLC and has IR: 5.68μ.

EXAMPLE 7

Utilizing suitable starting materials and substantially repeating the procedures described in Preparations A–F and Examples 1–6, there are produced the following compounds of the invention:

(5R,6S,8R,1'R)-6-(1-hydroxyethyl)-2-[(1'-amino-2'-methylthio)ethyl]-2-penem-3-carboxylic acid;
(5R,6S,8R,1'R)-6-(1-hydroxyethyl)-2-[(1'-amino-2'-hydroxy)ethyl]-2-penem-3-carboxylic acid;
(5R,6S,8R,1'R)-6-(1-hydroxyethyl)-2-[(1'-amino-2'-carboxy)ethyl]-2-penem-3-carboxylic acid;
(5R,6S,8R,1'R)-6-(1-hydroxyethyl)-2-[(1'-amino-2'-amino)ethyl]-2-penem-3-carboxylic acid;
(5R,6S,8R,1'R)-6-(1-hydroxyethyl)-2-[(1'-amino-2'-methylthioethyl]-2-penem-3-carboxylic acid;
(5R,6S,8R)-6-(1-hydroxyethyl)-2-[(1'-aminomethyl]-2-penem-3-carboxylic acid;
(5R,6S,8R,1'R)-6-(1-hydroxyethyl)-2-[(1'-amino-1'-carboxy)methyl]-2-penem-3-carboxylic acid;
(5R,6S,8R,1'R)-6-(1-hydroxyethyl)-2-[(1'-amino-3'-hydroxy)propyl]-2-penem-3-carboxylic acid;
(5R,6S,8R,1'R)-6-(1-hydroxyethyl)-2-[(1'-amino-3'-amino)propyl]-2-penem-3-carboxylic acid;
(5R,6S,8R,1'R)-6-(1-hydroxyethyl)-2-[(1'-amino-3'-ethylthio)propyl]-2-penem-3-carboxylic acid;
(5R,6S,8R,1'R)-6-(1-hydroxyethyl)-2-[(1'-amino-4'-hydroxy)butyl]-2-penem-3-carboxylic acid;
(5R,6S,8R,1'R)-6-(1-hydroxyethyl)-2-[(1'-amino-4'-carboxy)butyl]-2-penem-3-carboxylic acid;
(5R,6S,8R,1'R)-6-(1-hydroxyethyl)-2[(1'-amino4'-amino)butyl]-2-penem-3-carboxylic acid;
(5R,6S,8R,1'R)-6-(1-hydroxyethyl)-2-[(1'-amino-4'-methylthio)butyl]-2-penem-3-carboxylic acid;
(5R,6S,8R,1'R)-6-(1-hydroxyethyl)-2-[(1'-amino-4'-ethylthio)butyl]-2-penem-3-carboxylic acid;
(5R,6S,8R,1'R)-6-(1-hydroxyethyl)-2-[(1'-amino)propyl]-2-penem-3-carboxylic acid;
(5R,6S,8R,1'R)-6-(1-hydroxyethyl)-2-[(1'-amino)butyl]-2-penem-3-carboxylic acid;
(5R,6S,8R,1'R)-6-(1-hydroxyethyl)-2-[(1'-amino)pentyl]-2-penem-3-carboxylic acid;
(5R,6S,8R,1'R)-6-(1-hydroxyethyl)-2-[(1'-amino-5'-amino)pentyl]-2-penem-3-carboxylic acid;
(5R,6S,8R,1'R)-6-(1-hydroxyethyl)-2-[(1'-amino-5'-hydroxy)pentyl]-2-penem-3-carboxylic acid;
(5R,6S,8R,1'R)-6-(1-hydroxyethyl)-2-[(1'-amino-5'-carboxy)pentyl]-2-penem-3-carboxylic acid;
(5R,6S,8R,1'R)-6-(1-hydroxyethyl)-2-[(1'-amino-5'-methylthio)pentyl]-2-penem-3-carboxylic acid;
(5R,6S,8R,1'R)-6-(1-hydroxyethyl)-2-[(1'-amino-5'-ethylthio)pentyl]-2-penem-3-carboxylic acid;
(5R,6S,8R,1'R)-6-(1-hydroxyethyl)-2-[(1'-amino-6'-amino)hexyl]-2-penem-3-carboxylic acid;
(5R,6S,8R,1'R)-6-(1-hydroxyethyl)-2-[(1'-amino-6'-carboxy)hexyl]-2-penem-3-carboxylic acid;
(5R,6S,8R,1'R)-6-(1-hydroxyethyl)-2-[(1'-amino-6'-hydroxy)hexyl]-2-penem-3-carboxylic acid;
(5R,6S,8R,1'R)-6-(1-hydroxyethyl)-2-[(1'-amino-6'-amino)hexyl]-2-penem-3-carboxylic acid;
(5R,6S,8R,1'R)-6-(1-hydroxyethyl)-2-[(1'-amino)hexyl]-2-penem-3-carboxylic acid;
(5R,6S,8R,1'R)-6-(1-hydroxyethyl)-2-[1'-amino-2'-(4-imidazolyl)ethyl]-2-penem-3-carboxylic acid;
(5R,6S,8R,1'R)-6-(1-hydroxyethyl)-2-[(1'-amino-2'-phenyl)ethyl]-2-penem-3-carboxylic acid;
(5R,6S,8R,1'R)-6-(1-hydroxyethyl)-2-[(1'-amino-2'-p-hydroxyphenyl)ethyl]-2-penem-3-carboxylic acid;
(5R,6S,8R,1'R)-6-(1-hydroxyethyl)-2-[(1'-amino-2'-indolyl)ethyl]-2-penem-3-carboxylate.
(5R,6S,8R,1'R)-Sodium-6-(1-hydroxyethyl)-2-[1'-amino-3'-methylthio)propyl]-2-penem-3-carboxylate;
(5R,6S,8R,1'R)-Potassium-6-(1-hydroxyethyl)-2-[1'-amino-3'-methylthio)ethyl]-2-penem-3-carboxylate;
(5R,6S,8R,1'R)-Potassium-6-(1-hydroxyethyl)-2-[1'-amino-2'-methylthio)ethyl]-2-penem-3-carboxylate;

In the following Examples 11–15, the active ingredient may be (5R,6S,8R,1'R)-6-(1-hydroxyethyl)-2-[(1'-amino-3'-methylthio)propyl]-2-penem-3-carboxylic acid, (5R,6S,8R,1'R)-6-(1-hydroxyethyl)-2-[(1'-amino-3'-carboxy)propyl]-2-penem-3-carboxylic acid or an equivalent amount of any of the other compounds of this invention.

EXAMPLE 11

| No. | Ingredient | Capsules mg/capsule | mg/capsule |
|---|---|---|---|
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
| | Total | 500 | 650 |

Method of Manufacture

Mix Items Nos. 1, 2, 3 and 4 in a suitable mixer for 10–15 minutes. Add Item No. 5 and mix for 1–3 minutes.

Fill the mixture into suitable two-piece hard gelatin capsules using encapsulating machine.

EXAMPLE 12

| No. | Ingredient | mg/tablet | mg/tablet |
|---|---|---|---|
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Item Nos. 1 and 2 in a suitable mixer for 10–15 minutes. Granulate the mixture with Item No. 3. Past the wet granulation through a coarse screen (e.g. ¼") if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 13

| Injectable Powder: (per vial) | g/vial | g/vial |
|---|---|---|
| Active Ingredient | 0.5 | 1.0 |

Add sterile water for injection or bacteriostatic water for injection for reconstitution.

EXAMPLE 14

| Injectable Solution Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion ( 85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22μ membrane and fill into appropriate containers.
6. Terminally sterilize the units by autoclaving.

EXAMPLE 15

| Injectable Powder: (per vial) | g/vial |
|---|---|
| Active Ingredient | 1.0 |
| Sodium Citrate | 0.05 | pH is adjusted to 6.2 using 0.1N citric acid solution.

Add sterile water for injection or bacteriostatic water for injection for reconstitution.

What is claimed is:

1. A compound of the formula $$\begin{array}{c}\text{OH} \;\; H \;\; H \quad\quad\quad\quad NR'R'' \\ H_{\underset{CH_3}{\vert}}\!\!\!\diagdown\!\!\!\diagup\!\!\!\!\!\diagup\!\!\!\!\!-\!\!\!\!\!-\!\!\!\!S\!\!\!\diagdown \\ \quad\quad O\!\!=\!\!\diagdown\!-\!N\!-\!\!\!\diagup\!\!\!\!\diagdown\!(CH_2)_n\!\diagdown\!Z \\ \quad\quad\quad\quad\quad\quad COOH \end{array}$$

wherein n is 0–4;

R' and R" are indpendently hydrogen, lower alkyl, lower alkenyl, phenyl, substituted phenyl, wherein the substituents are one or more groups selected from chloro, bromo, fluoro, lower alkyl, hydroxy, nitro, amino, aminomethyl, lower monoalkylamino, lower dialkylamino, lower alkoxy and carboxy, or heteroaryl of 5 to 7 ring atoms of which 3 to 6 are carbon atoms and the remaining ring atoms are nitrogen, sulfur or oxygen, or R' is hydrogen and R" is $CH_3(CH_2)_pCO-$ or $CH_3(CH_2)_qSO_2-$, wherein p is 0–16 and q is 1–17, or R', R" and the N to which they are attached form a group of the formula $$-NR'-\underset{\underset{NR''}{\|}}{C}-X,$$

wherein X is hydrogen, lower alkyl or amino;

Z is hydrogen, COOR', OR', NR'R", SR', 4-imidazolyl, 3-indolyl, phenyl, p-hydroxyphenyl or branched lower alkyl, and the pharmaceutically acceptable salts and metabolizable esters thereof, in racemic or optically active form.

2. A compound of claim 1 of the formula $$\begin{array}{c}\text{OH} \;\; H \;\; H \quad\quad\quad\quad NH_2 \\ \diagdown\!\!\!\!\diagup\!\!\!\!\diagup\!\!\!\!\!-\!\!\!\!S\!\!\!\diagdown \\ \quad\quad O\!\!=\!\!\diagdown\!-\!N\!-\!\!\!\diagup\!\!\!\!\diagdown\!(CH_2)_n\!\diagdown\!Z \\ \quad\quad\quad\quad\quad\quad COOH \end{array}$$

wherein n is 0–4;

Z is hydrogen, carboxy, hydroxy, (lower)alkylthio or an amino group, and the pharmaceutically acceptable salts and metabolizable esters thereof, in racemic or optically active form.

3. A compound according to claim 1 wherein n is 1.

4. A compound according to claim 1 wherein Z is a carboxy group.

5. A compound according to claim 1 wherein Z is a (lower)alkylthio group.

6. A compound according to claim 1 wherein Z is a methylthio group.

7. A compound according to claim 1 wherein Z is an amino group.

8. A compound according to claim 1 wherein Z is a hydroxy group.

9. A compound according to claim 1 wherein Z is hydrogen.

10. A compound according to claim 2 wherein n is 0.

11. A compound according to claim 2 wherein n is 1.

12. A compound according to claim 2 wherein n is 3.

13. The compound according to claim 2 which is (5R,6S,8R,1′R) 6-(1-hydroxyethyl)-2-(1′-aminoethyl)-2-penem-3-carboxylic acid.

14. The compound according to claim 2 which is (5R,6S,8R,1′R) 6-(1-hydroxyethyl)-2-[(1′-amino-3′-carboxy)propyl]-2-penem-3-carboxylic acid.

15. The compound according to claim 2 which is (5R,6S,8R,1′R) 6-(1-hydroxyethyl)-2-[(1′-amino-3′-methylthio)propyl]-2-penem-3-carboxylic acid.

16. The compound according to claim 2 which is (5R,6S,8R,1′R) 6-(1-hydroxyethyl)-2-[(1′-amino-2′-methylthio)ethyl]-2-penem-3-carboxylic acid.

17. The compound according to claim 2 which is (5R,6S,8R,1′R) 6-(1-hydroxyethyl)-2-(1′,5′-diaminopentyl)-2-penem-3-carboxylate acid.

18. The compound according to claim 1 which is (5R,6S,8R,1′R) 6-(1-hydroxyethyl)-2-[(1′-acetimidoyl-3′-methylthio)propyl]-2-penem-3-carboxylate, sodium salt.

19. The compound according to claim 1 which is (5R,6S,8R,1′R) 6-(1-hydroxyethyl)-2-[(1′-guanidoyl-3′-methylthio)propyl]-2-penem-3-carboxylate, sodium salt.

20. A pharmaceutical composition comprising an effective amount of an antibacterial compound of claim 1 in admixture with a pharmaceutically acceptable carrier therefor.

21. A pharmaceutical composition according to claim 20 wherein said compound is (5R,6S,8R,1′R) 6-(1-hydroxyethyl)-2-[(1′-amino-3′-methylthio)propyl]-2-penem-3-carboxylic acid.

22. A composition according to claim 20 adapted for oral administration.

23. A composition according to claim 20 adapted for parenteral administration.

24. A composition according to claim 20 adapted for topical administration.

25. A method of treating or preventing bacterial infections in animals which comprises administering a compound of claim 1 or a pharmaceutical composition thereof, to an infected host in an amount sufficient to treat or prevent such infection.

26. A method according to claim 25 wherein the route of administration is oral.

27. A method according to claim 25 wherein the route of administration is parenteral.

28. A method according to claim 25 wherein the route route of administration is topical.

29. A method according to claim 25 wherein said compound is (5R,6S,8R,1′R) 6-(1-hydroxyethyl)-2-[(1′-amino-3′-methylthio)propyl]-2-penem-3-carboxylic acid.

* * * * *